(12) United States Patent
Sandvick (10) Patent No.: US 8,747,775 B2
(45) Date of Patent: Jun. 10, 2014

(54) FOOD SAFETY INDICATOR

(75) Inventor: Warren Sandvick, Lubbock, TX (US)

(73) Assignee: Food Technologies International, LLC, Lubbock, TX (US)

( * ) Notice: Subject to any disclaimer, the term of this patent is extended or adjusted under 35 U.S.C. 154(b) by 0 days.

(21) Appl. No.: 13/493,728

(22) Filed: Jun. 11, 2012

(65) Prior Publication Data

US 2012/0274470 A1 Nov. 1, 2012

Related U.S. Application Data (63) Continuation-in-part of application No. PCT/US2010/060116, filed on Dec. 13, 2010.

(60) Provisional application No. 61/285,622, filed on Dec. 11, 2009.

(51) Int. Cl.
*G01N 31/22* (2006.01)

(52) U.S. Cl.
USPC ............. 422/404; 422/105; 426/87; 426/383; 436/180

(58) Field of Classification Search
USPC ............. 422/404, 500–503, 105; 340/539.27; 426/87, 383; 436/180
See application file for complete search history.

(56) References Cited

U.S. PATENT DOCUMENTS

| | | | |
|---|---|---|---|
| 4,003,709 A | 1/1977 | Eaton et al. | |
| 4,292,916 A | 10/1981 | Bradley et al. | |
| 5,045,283 A | 9/1991 | Patel | |
| 5,053,339 A | 10/1991 | Patel | |
| 6,737,274 B1 | 5/2004 | Wright | |
| 7,514,899 B2 * | 4/2009 | Deng-Peng | 320/101 |

(Continued)

FOREIGN PATENT DOCUMENTS

| | | |
|---|---|---|
| KR | 20090014874 A | 2/2009 |
| WO | WO-2008006152 A1 | 1/2008 |

OTHER PUBLICATIONS

"Fraunhofer ENAS presents a printed battery at the nano tech exhibition in Tokyo," Press Release, www.enas.fraunhofer.de, Jan. 15, 2009, Fraunhofer Research Institution for Electronic Nano Systems ENAS, 1 page.

(Continued)

*Primary Examiner* — Jyoti Nagpaul
(74) *Attorney, Agent, or Firm* — Blank Rome LLP (57) ABSTRACT

A food safety device for placement on a product is disclosed. The food safety device comprises one or more sensors that measure at least one condition of the product and/or its environment, one or more visual indicators that are configured to display a visual indication of freshness and/or safety of the product. An antenna transmits and receives data regarding the at least one measured condition of the product and the freshness and/or safety of the product. A logic module executes programmable logic to determine the freshness and/or safety of the product from the at least one measured condition of the product, to cause the one or more visual indicators to display a visual indication of the freshness and/or safety it determines, and to transmit and receive data regarding the at least one measured condition of the product and the freshness and/or safety of the product via the antenna.

19 Claims, 5 Drawing Sheets

(56) References Cited

U.S. PATENT DOCUMENTS

| | | | |
|---|---|---|---|
| 7,643,378 | B2 | 1/2010 | Genosar |
| 7,675,409 | B2 * | 3/2010 | Jensen et al. ............... 340/539.1 |
| 7,675,424 | B2 | 3/2010 | Debord et al. |
| 7,764,183 | B2 | 7/2010 | Burchell et al. |
| 8,014,234 | B2 | 9/2011 | Braunberger |
| 8,077,553 | B2 | 12/2011 | Braunberger |
| 2002/0118106 | A1 | 8/2002 | Brenn |
| 2003/0219648 | A1 | 11/2003 | Zucker |
| 2005/0248455 | A1 * | 11/2005 | Pope et al. ............... 340/539.27 |
| 2006/0145863 | A1 | 7/2006 | Martin et al. |
| 2007/0203650 | A1 | 8/2007 | Jensen et al. |
| 2007/0273507 | A1 | 11/2007 | Burchell et al. |
| 2008/0204246 | A1 | 8/2008 | Kates |
| 2008/0272131 | A1 | 11/2008 | Roberts et al. |
| 2009/0277199 | A1 | 11/2009 | Manas et al. |
| 2011/0135697 | A1 | 6/2011 | Omenetto et al. |
| 2011/0223153 | A1 | 9/2011 | Lu et al. |
| 2012/0034291 | A1 | 2/2012 | Amsden et al. |

OTHER PUBLICATIONS

J. Bryner, "Bendable Antennas Could Reshape Electronics," LiveScience, http://www.livescience.com/technology, Nov. 30, 2009, 2 pages.

A. Danigelis, "Edible Gold Sensors Alert to Spoiled Food," www.news.discovery.com/tech/edible-gold-sensors-alert-to-spoiled-food-120306.html, Mar. 6, 2012, 2 pages.

F. Braunberger, "Time Dependent—Temperature Independent Color Changing Label: Replaceing the Printed-On Expiration Date," Vision Works IP Corp., www.fritz@visionworksip.com, Jan. 30, 2009, 7 pages.

"Your Dinner Has Been Touched by Multitudes," Bloomberg Businessweek, Aug. 29-Sep. 4, 2011, 2 pages.

"What is ScoringAG?," www.scoringag.com//scoringag/3/index.cfm?sfa=main.main, Sep. 25, 2011, 1 page.

Internation Preliminary Report dated Sep. 16, 2011, cited in International Application No. PCT/US2010/060116.

N Wang et al., "Wireless Sensors in Agriculture and Food Industry—Recent Development and Future Perspective," vol. 50. No 1. Jan. 2006. pp. 1-14.

* cited by examiner

FIGURE 3B

FOOD SAFETY INDICATOR

CROSS-REFERENCE TO RELATED APPLICATIONS

This application is a continuation-in-part of PCT/US2010/060116 (WO2011/072296), filed Dec. 13, 2010, which claims the benefit of U.S. Provisional Application No. 61/285,622, filed Dec. 11, 2009. The entire contents of those applications are hereby incorporated by reference.

BACKGROUND OF THE INVENTION

1. Field of the Invention

The present invention relates to an apparatus and method for indicating whether products are safe for consumption. More particularly, the present invention relates to an apparatus and method that not only identifies whether products are safe for consumption, but that also tracks the source, location, and destination of those products so they can be efficiently and effectively identified and recalled if and when they are not safe for consumption.

2. Background of the Related Art

The term "perishable" is used to refer to products that are subject to spoilage or decay. Such products have a measurable shelf-life, after which the product is no longer safe to use or consume. Perishable products include, but are not limited to, chilled and minimally processed foods and beverages, pharmaceuticals, chemicals, film, batteries, munitions, and even blood, each of which has its own unique shelf-life. Accordingly, the companies that make and/or sell those products are presented with the continuing problem of identifying which products have exceeded their shelf-life. And as a result, those companies not only have difficulty preventing the sale of perishable products that have exceeded their shelf-life, they also have significant difficulty recalling those products after they are sold. Similar difficulties arise when identifying food that has not exceeded its shelf-life but that is otherwise tainted or contaminated, such as by poor manufacturing, transportation, or storage conditions.

The inability to efficiently and effectively identify and recall spoiled or contaminated products is not only a serious problem for the companies that make and/or sell those products, it is a potentially life-threatening problem to the end users of those products (i.e., the people who consume those products). In 2010, for example, outbreaks of food poisoning involving products as varied as eggs, peanuts, and spinach sickened thousands of people and killed more than a dozen people. In 2008, a salmonella outbreak from contaminated peanut butter manufactured under unsanitary conditions sickened hundreds of people and may have killed as many as eight people. And in 2004, an arthritis drug was discovered to increase the risk of heart attacks and strokes in people who took the drug for at least eighteen months, for which the manufacturer of the drug ultimately paid $4.85 billion to settle 27,000 resulting lawsuits.

As those examples illustrate, the inability to efficiently and effectively identify and recall spoiled or contaminated products can not only cost the companies that make those products significant amounts of money, it can also harm the end users of those products. As a result, there is a need for an apparatus and method that not only identifies whether products are safe for consumption, but that also tracks the source, location, and destination of those products so they can be efficiently and effectively identified and recalled when they are not safe for consumption.

SUMMARY OF THE INVENTION

Accordingly, it is an object of the invention to provide a food safety device that not only identifies whether products are safe for consumption, but that also tracks the source, location, and destination of those products so they can be efficiently and effectively identified and recalled when they are not safe for consumption. The food safety device comprises one or more sensors that are configured to measure at least one condition of the product and/or its environment, one or more visual indicators that are configured to display a visual indication of freshness and/or safety of the product, an antenna that is configured to transmit and receive data regarding the at least one measured condition of the product and the freshness and/or safety of the product, and a logic module that is configured to execute programmable logic to determine the freshness and/or safety of the product from the at least one measured condition of the product, to cause the one or more visual indicators to display a visual indication of the freshness and/or safety it determines, and to transmit and receive data regarding the at least one measured condition of the product and the freshness and/or safety of the product via the antenna. Those and other objects, advantages, and features of the present invention will become more readily apparent by the following written description, taken in conjunction with the accompanying drawings and claims.

BRIEF DESCRIPTION OF THE DRAWINGS

Many aspects of the present invention can be better understood with reference to the accompanying drawings, which are part of the specification and represent exemplary embodiments of the present invention. The components in the drawings are not necessarily to scale, emphasis instead being placed upon illustrating the principles of the present invention. And in the drawings, like reference numerals designate corresponding parts throughout the several views.

DETAILED DESCRIPTION OF THE PREFERRED EMBODIMENTS

In describing the preferred embodiments of the present invention illustrated in the drawings, specific terminology will be resorted to for the sake of clarity. However, the present invention is not intended to be limited to the specific terms so selected, and it is to be understood that each specific term includes all technical equivalents that operate in a similar manner to accomplish a similar purpose.

The present invention provides an inexpensive apparatus and method for identifying whether products are safe for consumption. For example, the present invention can determine whether a perishable product has exceeded its shelf-life based on a chemical reaction with the product that measures the spoilage/decay of the product. See, e.g., U.S. Pat. No. 4,003,709 to Eaton et al. ("the '709 patent"). The present invention can determine whether a perishable product has exceeded its shelf-life based on a time- and/or temperature-dependent chemical reaction that is initiated by a predefined condition, such as packaging the product or opening the product. See, e.g., U.S. Pat. No. 7,643,378 to Genosar ("the '378 patent"), U.S. Pat. No. 6,737,274 to Wright ("the '274 patent"), U.S. Pat. No. 5,053,339 to Patel ("the '339 patent"), U.S. Pat. No. 5,045,283 to Patel ("the '283 patent"), and U.S. Pat. No. 4,292,916 to Bradley et al. ("the '916 patent"). Or the present invention can determine whether a perishable product has exceeded its shelf-life based on a time- and/or temperature-dependent circuit that is configured to measure time and/or temperature differences. See, e.g., U.S. Pat. No. 7,675,424 to Debord et al. ("the '424 patent") and U.S. Pat. No. 7,764,183 to Burchell et al. ("the '183 patent"). The contents of the '709 patent, the '378 patent, the '274 patent, the '339 patent, the '283 patent, the '916 patent, the '424 patent, and the '183 patent are hereby incorporated by reference as if fully set forth herein.

The present invention can also determine whether a perishable product has exceeded its shelf-life by chemically and/or electronically measuring exposure to moisture, sunlight, radiation, or any other environmental factor that can contribute to spoilage and reduce a perishable product's shelf-life. In a similar manner, the present invention can chemically or electronically measure the amount of hazardous chemicals, toxins, food borne pathogens, and other contaminants that may be present in a product and make it unsafe for use and/or consumption. The present invention includes at least one of a visual, tactile, and audible indicator to identify when a product has exceeded its shelf-life or contains an unsafe level of contaminants.

In addition, the present invention includes functionality for tracking the source, location, and destination of products at various points during their life cycle (e.g., manufacture, distribution, sale, etc). When used in conjunction with the functionality for identifying exceeded shelf-life and/or contaminants, that functionality allows products to be efficiently and effectively identified and recalled when they are identified as not being safe for consumption. Moreover, it allows the point in the life cycle of a product at which any problems occurred to be identified and remedied. Accordingly, the present invention not only allows products to be efficiently and effectively identified and recalled when they not safe for consumption, it also allows the source of any contributing factors to be quickly identified and remedied.

Figure 1A:
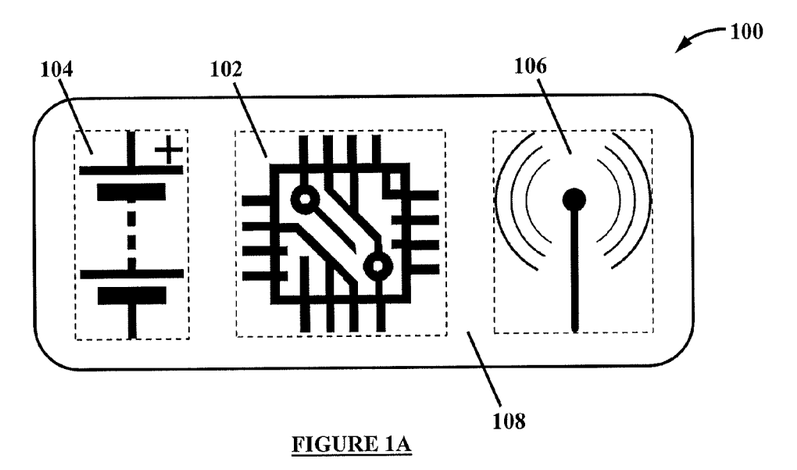
FIG. 1A is a plan view illustrating a non-limiting embodiment of the internal components of a food safety device according to the present invention.
Figure 1B:
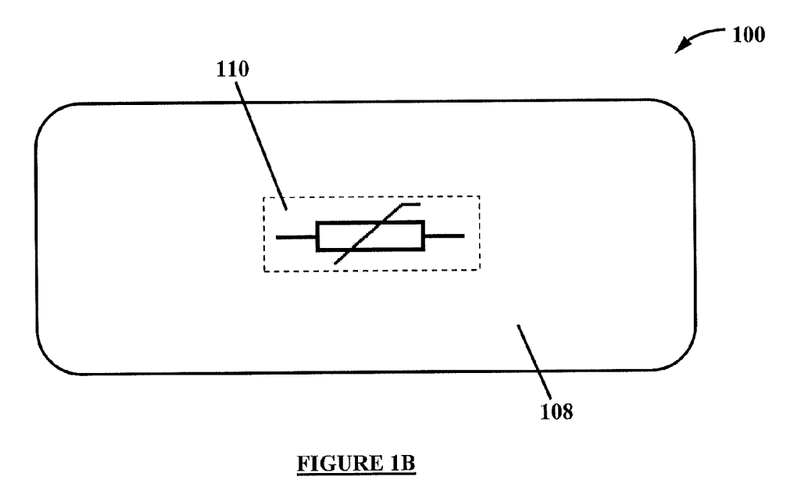
FIG. 1B is a plan view illustrating a non-limiting embodiment of the rear face of a food safety device according to the present invention.
Figure 1C:
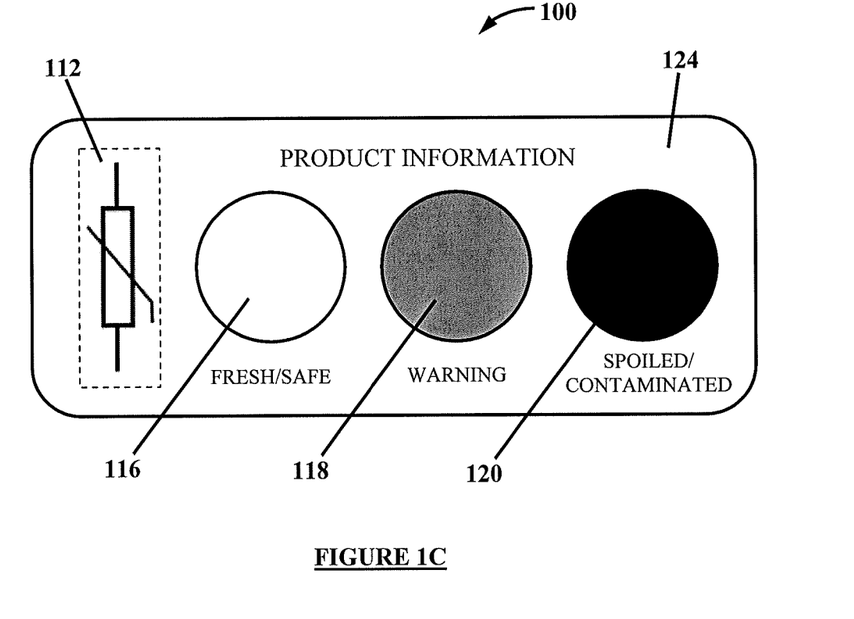
FIGS. 1C-1E are plan views illustrating different non-limiting embodiments of the front face of a food safety device according to the present invention.
Figure 1D:
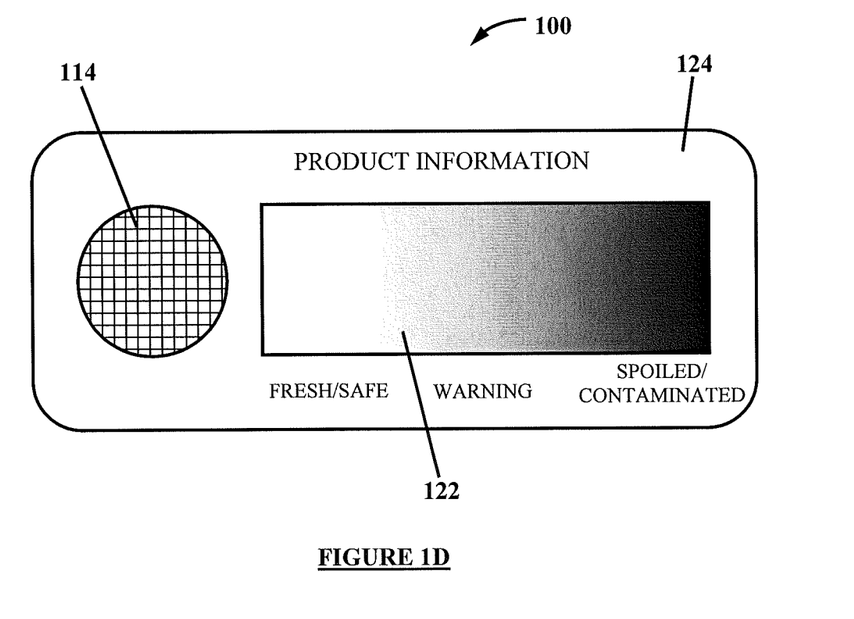
Figure 1E:
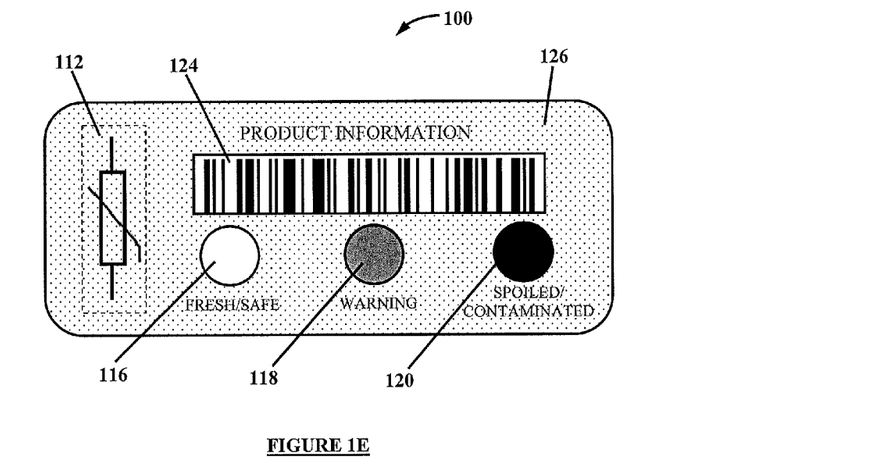

Turning to the drawings, FIGS. 1A-1E illustrate an exemplary embodiment of a food safety device 100 according to the present invention. FIG. 1A illustrates the internal workings of the food safety device 100. FIG. 1B illustrates the rear face of the food safety device 100. And FIGS. 1C-1E illustrate different embodiments of the front face of the food safety device 100. The food safety device 100 is preferably small in size and substantially flat so it can be adhered to, fastened to, or otherwise attached to a product or its packaging without interfering with the handling, packaging, or use of the product. For example, the food safety device may be the size of and/or incorporated into a conventional label for a product (e.g., the label on a jar, a bottle of medicine, a box of film, or directly on the product).

As FIG. 1A illustrates, the food safety device 100 includes a logic module 102, a battery 104, and an antenna 106. The logic module 102 includes a data storage device that is configured to store data about a product and/or a product container as well as the product's environment throughout the product's life cycle, programmable logic that is configured to monitor the shelf-life and/or contamination of the product as well as the product's environment throughout the product's life cycle, and a processor and/or integrated circuitry configured to execute the programmable logic so the food safety device 100 can be used in the manner disclosed herein. The battery 104 provides power to the logic module 102 and the antenna 106 so they can be operated in the manner disclosed herein. And the antenna 104 allows the logic module 102 to wirelessly communicate data with external devices in the manner disclosed herein. Preferably, the logic module 102, battery 104, and antenna 106 utilize micro- and/or nano-technology so they can be discretely assembled substantially flat within a product label without interfering with the handling, packaging, and/or use of the product and/or product container on which that label is placed.

For example, the battery 104 may be a printed battery, such as the thin printed battery developed by the Fraunhofer Research Institution for Electronic Nano Systems ENAS. See, e.g., "Fraunhofer ENAS presents a printed battery at the nano tech exhibition in Tokyo", Press Release, www.enas.fraunhofer.de (Jan. 15, 2009). And the antenna 106 may be a thin (e.g., several millimeters), bendable, self-healing antenna, such as the antenna developed by researchers as the North Carolina State University. See, e.g., Bryner, Jeanna, "Bendable Antennas Could Reshape Electronics", LIVE-SCIENCE, http://www.livescience.com/technology (Nov. 30, 2009). Such printed batteries and flexible antennae are particularly suited for small, thin, and flexible applications, such as product labels.

The logic module 102, the battery 104, and the antenna 106 are printed on, bonded to, or otherwise attached to the front face of a flexible backing sheet 108. Those components are electrically connected to each other, as well as to various sensors 110 (FIG. 1B), 112 (FIGS. 1C and 1E), and 114 (FIG. 1D) and visual indicators 116-120 (FIG. 1C and 1E), 122 (FIG. 1D), and 124 (FIG. 1E) by a series of conductors, such as copper traces (not shown), printed on, bonded to, or otherwise attached to the front face of the flexible backing sheet 108. The rear face of the flexible sheet 108 includes an adhesive or other suitable attachment mechanism for attaching the food safety device 100 to a product, packaging and/or product container. And as FIG. 1B illustrates, the rear face of the flexible sheet 108 may also include one or more sensors 110. The sensors 110 can be free of adhesive so that the adhesive does not interfere with the operation of the sensors 110. Or, the adhesive can be provided on the sensors 110 to better directly attach the sensors 110 to the product, container or packaging.

One or more sensors 110 may be provided on the rear face of the flexible backing sheet 108, and therefore on the rear face of the food safety device 100, to monitor one or more conditions of the product and/or product container on which the food safety device 100 is placed. Those sensors 110 are preferably located on the rear face of the food safety device 100 so they will be in closer proximity to the product and/or product container and, therefore, will obtain more accurate measurements on the condition of the product and/or product container. When the food safety device 100 is placed directly on the product, at least one of the sensors 110 on the rear face may be configured to protrude into the product or to sit flush with the outer surface of the product. And when the food safety device 100 is placed on the product container, at least one of the sensors 110 may be configured to protrude through the product container and into the product or to sit flush with the outer surface of the product container. A sensor 110 may protrude into the product to measure conditions that indicate spoilage (e.g., core temperature, PH level, etc.) and/or conditions that indicate contamination (e.g., the presence of certain chemicals or bacteria, a pressure change in the container, etc.). And a sensor 110 may sit flush with the outer surface of the product or product container to measure similar conditions that do not need to be obtained internally (e.g., surface temperature, breakage of the container, etc.). The sensors 110 can operate based on chemical and/or electrical reactions to the condition being measured. Moreover, by measuring multiple conditions, the food safety device 100 can more accurately determine the remaining shelf-life of a product and/or identify contaminants.

For example, by measuring the temperature of a product as well as the time that the product has been in its container, the logic module 102 of the food safety device 100 can actively determine the remaining shelf-life of the product. As temperatures increase during the product's life cycle, the shelf-life of the product may decrease. And as the shelf-life of a product decreases, the time from when the product was placed in its container until the time at which it is safe for consumption is reduced. Accordingly, the logic module 102 can either speed up a clocking circuit or subtract time from the estimated shelf-life of a product based on temperature fluctuations. In that way, the food safety device 100 will indicate that the product has exceeded its shelf-life earlier than a product that did not experience the same temperature increases. The logic module 102 can also store data identifying the time, date, and amount of such temperature increases to create an ongoing log of the product's condition throughout its life cycle.

The antenna 106 can also be used as a sensor. For example, the food safety device 100 will expand or contract with the product and/or product container to which it is attached during temperature changes or pressure changes when the food safety device 100 is adhered to that product and/or product container. And when the antenna 106 is a flexible antenna, as disclosed above, it will also expand and contract as the food safety device 100 expands and contracts. Such stretching will change the frequency of the antenna slightly, and those frequency changes can be directly correlated to temperature changes and/or pressure changes. Thus, the antenna 106 can be used to measure temperature and/or pressure fluctuations in the same manner as a strain gauge.

And as FIGS. 1C and 1D illustrate, one or more sensors 112 and 114 may also be placed on the front face of the food safety device 100 to perform similar functions as the sensors 110 on the rear face of the food safety device 100. However, the sensors 112 and 114 on the front face of the food safety device are preferably configured to measure one or more environmental conditions rather one or more conditions of the product and/or product container. For example, a sensor 112 (FIGS. 1C and 1E) on the front face of the food safety device 100 may be used to measure the temperature, barometric pressure, light exposure, and humidity of the various environments in which the product and/or product container are present during its life cycle (e.g., assembly line, warehouse, store shelf, etc.). That sensor 112, or another sensor (not shown), on the front face may also measure any vibration, shock, acceleration, radiation (such as a Geiger counter), hazardous chemicals, toxins, or food borne pathogens to which the product and/or container are exposed during its life cycle. The logic module 102 can store data identifying the time, date, and amount in which each of those conditions occurred to create an ongoing log of the product's environment throughout its life cycle.

The logic module 102 can also use those environmental measurements to determine the shelf-life of the product and/or identify contamination in a similar manner to that disclosed above with respect to the sensors 110 on the rear face of the food safety device. Moreover, by using the environmental measurements taken at the front face of the food safety device 100 in conjunction with the product conditions measured at the rear face of the food safety device 100, the shelf-life of the product and/or contamination of the product can be determined more accurately and in more ways. For example, if a quick change of temperature and/or pressure is measured at the product and/or product container but not in the environment in which the product and/or product container is present, the logic module 102 may determine that the product container has been opened and/or tampered with, which might result in a pressure loss and/or temperature change in the product container (e.g., opening a pressure-sealed container). Moreover, by logging both the environmental measurements and the product condition measurements, those measurements can be compared to each other to identify any potentially erroneous readings.

A light sensor 114 (FIG. 1D), such as a photovoltaic solar cell, may also be provided on the front face of the food safety device 100 to measure the amount of sunlight to which the product and/or product container are exposed. As with temperature, increased exposure to sunlight may also decrease the shelf-life of a product. Sunlight may also deteriorate a product container over time. Accordingly, the logic module 102 can use the amount of sunlight exposure measured with the light sensor 114 in conjunction with time and temperature measurements to more accurately calculate a product and/or product container's shelf-life. The light sensor 114 may also be used to charge the battery 104 or to replace it as a power source for the other components of the food safety device 100.

As FIGS. 1C-1E illustrate, a series of visual indicators 116-120 or a single sliding scale visual indicator 122 can also be disposed on the front face of the food safety device 100 to indicate product freshness and/or safety. Those visual indicators 116-124 can be provided in the form of a chemical strip (see, e.g., the '274 patent, the '339 patent, and the '283 patent), a light emitting diode (LED) or a liquid crystal display (LCD) (see, e.g., '424 patent and the '183 patent), or any other suitable visual indicator. The series of visual indicators 116-120 can be different colors with each color representing a different level of product freshness and/or safety. And the sliding scale visual indicator 122 can progressively illuminate or change color to represent different levels of product freshness and/or safety. For example, the first visual indicator 116 will display a green color when the product is fresh and/or not contaminated. The second visual indicator 118 will display a yellow color when the product has experienced some condition that may contribute to spoilage or contamination (e.g., passage of time, temperature change, etc.). And the third visual indicator 120 will display a red color when the product has spoiled and/or has been contaminated. Or, in the alternative, the sliding scale visual indicator 122 will gradually change from green to red as each of those conditions occurs.

When the visual indicators 116-124 are chemical strips, they can react like litmus paper to changes in the product's condition and/or changes in product's environment. For example, a time-release chemical reaction can be used to indicate the remaining shelf-life of the product. Or chemicals that react with specific toxins, radiation, and/or pathogens (e.g., *Salmonella* in meats) can be used to indicate if and when a product has been contaminated. Similarly, when the visual indicators are LEDs or LCDs, the measurements taken by the sensors 110-114 can be used by the logic module 102 in conjunction with a clocking circuit to determine the remaining shelf-life of a product and/or to identify if and when that product was contaminated. The reactions that occur in the chemical strips may also be detected and used by the logic module 102 to determine the remaining shelf-life of a product and/or to identify if and when that product was contaminated. And the logic module 102 can store all of that data, as well as the time and date at which it was recorded, to create an ongoing log of the product's condition and environment throughout the product's life cycle.

The chemical reaction that takes place in the battery 104 can also be used as an indicator of shelf-life. For example, the battery 104 can be sized such that its working life corresponds to the shelf-life of the product to which the food safety device 100 is attached. And as the battery 104 loses power, different visual indicators 116-122 can be illuminated and/or extinguished to indicate the freshness of that product. Thus, the battery 104 can be used in the same manner as a chemical strip with a time-release chemical reaction.

Preferably, when a series of visual indicators 116-120 is used, one visual indicator will stop displaying its respective color when another visual indicator begins displaying its respective color. In that way, an end user's attention will be more clearly drawn to the current condition of the product. And as yet another alternative, a visual indicator 124 may display a bar code that can be scanned to determine the different levels of product freshness and/or safety, as illustrated in FIG. 1E. In addition, instead of displaying different colors, the visual indicators 116-124 may display words or symbols that indicate the different levels of product freshness and/or safety. Such a display of information can be by a chemical reaction in a chemical strip or by illuminating an LED or LCD. The bar code can be displayed on the display and can change to indicate different information, such as the level of freshness.

In addition to visual indicators 116-124, the food safety device 100 may also include tactile indicators (e.g., a vibration device), audible indicators (e.g., a speaker), and/or a combination thereof (e.g., a buzzer) to indicate different levels of product freshness and/or safety. Such indicators would further serve to obtain the attention of a potential end user. But because such indicators might be bothersome if activated over long periods of time, they are preferably only used to indicate when a product has exceeded its shelf-life and/or has been contaminated. Moreover, if such indicators were used at other times, they would more rapidly exhaust the power of the battery 104, which is undesirable for products with longer life cycles.

And in addition to visual indicators 116-124, tactile indicators, and audible indicators, the logic module 102 may use the antenna 106 to wirelessly transmit a signal that indicates the different levels of product freshness and/or safety. Those signals are received by a computer that tracks the product on which the food safety device 100 is placed such that, when problems are detected, that product can be easily identified and removed from its life cycle before it is consumed. For example, if a product exceeds its shelf-life and/or becomes contaminated while sitting on a warehouse or retail store shelf, a signal will automatically be sent to an inventory system to identify that product for immediate removal from the shelf. In that way, unsafe products can be effectively and efficiently identified and recalled before they reach, and potentially harm, an end user.

As FIGS. 1C-1E also illustrate, the various sensors 112 and 114 and the various visual indicators 116-124 of the food safety device 100 are disposed on a flexible cover sheet 126. The sensors 112 and 114 can be disposed on the front face or the rear face of the flexible cover sheet 126. But because the light sensor 114 needs to be exposed to light, it is preferably disposed on the front face of the flexible cover sheet 126, which is exposed to the environment when the food safety device 100 is disposed on a product or product container. And when the other sensors 112 are disposed on the rear face of the flexible cover sheet 126, the flexible cover sheet 126 is preferably porous in the area adjacent to those sensors 112, as illustrated in FIG. 1E, so molecules can pass through the flexible cover sheet 126 to those sensors 112.

The visual indicators 116-124 are disposed on the front face of the flexible cover sheet 126 so they will be clearly visible to a user. Text that identifies what each indicator 116-120, or each location on each indicator 122, means (e.g., "Fresh", Safe", "Warning", "Spoiled", "Contaminated", etc.) can be printed on the flexible cover sheet 126 adjacent to each corresponding visual indicator 116-122. And because the food safety device 100 may double as a conventional product label, conventional product information may also be printed on the front face of the flexible cover sheet 126.

Figure 2A:
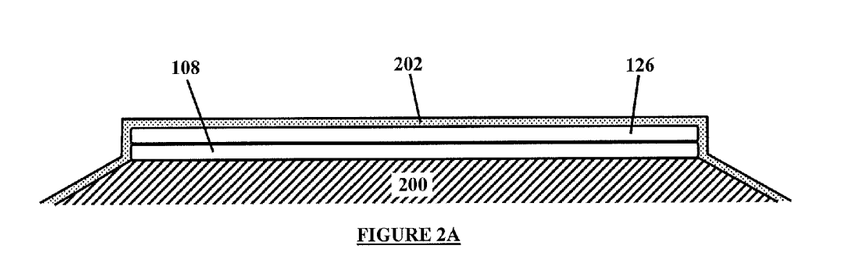
FIGS. 2A and 2B are elevation views illustrating non-limiting embodiments of the food safety device of FIGS. 1A-1E placed on a product or product packaging, respectively.
Figure 2B:
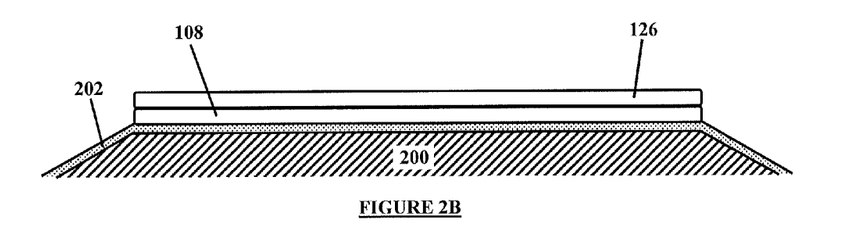

As FIGS. 2A and 2B illustrate, the rear face of the flexible cover sheet 126 is adhered to or otherwise attached to the front face of the flexible backing sheet 108 with the logic module 102, battery 104, and antenna 106 disposed therebetween. In that way, the logic module 102, battery 104, and antenna 106 are protected from the environment by the flexible backing sheet 108 and the flexible cover sheet 126. In the alternative, the flexible backing layer can be omitted and the logic module 102, battery 104, antenna 106, and their corresponding conductors can be disposed on the rear face of the flexible cover sheet 126. In that alternative embodiment, the logic module 102, battery 104, antenna 106, and their corresponding conductors can be protected from the environment by covering them with a layer of adhesive on the rear face of the flexible cover sheet 126.

When the flexible cover sheet 126 is placed on the flexible backing sheet 108, the various sensors 112 and 114 and the various visual indicators 116-124 are placed in electrical communication with the logic module 102, battery 104, and antenna 106. That electrical contact can be provided by contacts formed on the front face of the flexible backing sheet 108 in locations that correspond to the contacts of the sensors 112 and 114 and the visual indicators 116-124. The sensors 110 disposed on the rear face of the flexible backing sheet 108 are placed in electrical communication with the logic module 102, battery 104, and antenna 106 in a similar manner. In that way, the logic module 102, battery 104, antenna 106, sensors 110-114, and visual indicators 116-124 form a single, integrated circuit within the food safety device 100.

As discussed above, the food safety device 100 can be placed directly on a product 200 (FIG. 2A) or on a product container 202 (FIG. 2B). When the food safety device 100 is placed directly on the product 200, both the product 200 and the food safety device 100 may be placed in a product container 202. Depending on the material of which the product container 202 is formed, it may be porous and allow at least some small molecules to pass through it from the environment and into the product container 202 so the sensors 112 on the front face of the food safety device 100 can measure environmental conditions. However, the material of the product container 202 is unlikely to be so porous as to allow contaminants from the environment to enter the product container 202 that might spoil and/or contaminate the product 200. Instead, it may only be so porous as to allow very small molecules to enter the product container 202, just as helium can escape very slowly through the material of a balloon. Thus, in a similar manner, sensors 110 on the rear face of the food safety device 100 placed on the outside of the product container 202 may also be able to measure certain product conditions from molecules that pass from the product 200 through the product container 202 and into the food safety device 100.

As also discussed above, the various components of the food safety device 100 are preferably manufactured using micro- and/or nano-technology so they can be made thin, flexible, and small such that they can be attached to a product 200 and/or product container 202 without interfering with the manufacture, handling, and/or use of the product 200. And if the food safety device 100 is too thick in some applications, the product container 202 can be formed with a corresponding notch or opening that is configured to receive the food safety device 100 therein. Such a notch or opening can be configured to ensure the food safety device 100 does not interfere with the manufacture, handling, and/or use of the product 200.

In operation, the food safety device 100 of the present invention monitors the shelf-life and/or potential contamination of a product 200 throughout that product's life cycle (i.e., from manufacture to consumption). The logic module 102 can communicate with various external systems (e.g., an inventory system, a packaging machine, etc.) to exchange data about the product 200 and/or product container 202. That exchange of data allows the food safety device 100 of the present invention to accurately identify whether certain products 200 are safe for consumption and to track the source, location, and destination of those products so they can be efficiently and effectively identified and removed from their life cycle when they are not safe for consumption. Moreover, the data recorded by the food safety device 100 can be used to extrapolate and determine the expected shelf-life of a product 200 based on different events that occur during that product's 200 life cycle, which is extremely useful for purposes of inventory control (i.e., products with a shelf-life that will be exceeded sooner than that of other products can be distributed to the end user before those other products).

In order to exchange data with various external systems, the antenna 106 of the food safety device can be configured to send and receive data via radio frequency (RFID) (such as with an RFID reader) or other wireless technology, such as BLUE TOOTH brand wireless technology. The logic module 102 and antenna 106 may also be configured to emit and receive signals that identify the geographic location of the food safety device 100 and, therefore, the product 200 to which it is attached. Such location can be determined by transmitting and/or receiving geographic coordinates obtained with an internal and/or external global positioning system (GPS), or it can be determined by storing transmitting and/or receiving data that otherwise identifies the location of the product 200 (e.g., a shelf and/or aisle number). Along with time and date information, the food safety device 100 can use that location data to create an ongoing log of the product's 200 location throughout its life cycle. Moreover, that data allows the product 200 to be located and tracked in real time at any point throughout its life cycle, from origin to end user. That feature is particularly useful when the product 200 has been identified as unsafe for consumption and needs to be located for a recall.

The food safety device 100 can be programmed in a number of ways, such as by a preprogrammed microprocessor chip installed in the logic module 102 or flash programming the logic module 102 onsite. The programming of each food safety device 100 is matched to the specific product 200 to which it will be attached based on that product's 200 expected shelf-life and/or any potential types of contamination that might make that product 200 unsafe for consumption. Or each food safety device 100 can include programming for multiple different types of products 200 with the specific program to be executed by the logic module 102 being selected when the food safety device 100 is activated. In addition, the battery 104 can be programmed so that a separate logic module 102 need not be provided (i.e., the logic module may be integrated with the battery).

By way of example, the food safety device 100 could be programmed or preprogrammed for 6 days when used for bread. When the bread is packaged, a countdown timer in the logic module 102 would be activated. The food safety device 100 would indicate that the bread is fresh for the first 24 hours from the date of packaging. From 2-3 days, the food safety device 100 would indicate that the bread is still useable, but less fresh. From days 4-6, the food safety device 100 would indicate that the bread is starting to become stale. After 7 days, the food safety device 100 would indicate that the bread is possibly stale. In addition, if the humidity inside the package is high, the food safety device 100 would indicate that the bread is possibly moldy after 5 or 6 days.

In addition, the food safety device 100 can be configured for a number uses and can be incorporated in a number of different packaging methods for easy delivery on, to, or as part of the product container 202. For example, it may be attached as an adhesive strip during packaging, a tag, shrink wrap, or as part of the package material itself. In addition, the food safety device 100 can be printed directly onto the product container 202 and automatically start counting the time to expiration when it is printed. Accordingly, each product 200 preferably has its own food safety device 100 so that the freshness of that particular product 200 is easily determined. The food safety device 100 is preferably tamper-proof so that it cannot be removed without damaging the product 200 and/or product container 202 in a manner easily recognizable by the end user.

The food safety device 100 may also be activated in a number of ways. A product manufacturer/packager may activate the food safety device 100 at the time of production or packaging via battery activation, light activation, wireless activation, thermal activation, pressure activation, liquid activation, magnetic activation, or other activation technique. For example, the food safety device 100 can be activated by removing a pull strip to place the battery in electrical communication with the logic module 102 (i.e., battery activation); removing an adhesive paper from the light sensor 114 to expose it to light (i.e., light activation); sending an RFID or wireless signal to the logic module 102 via the antenna 106 (i.e., wireless activation); imparting a drastic temperature or pressure change on the food safety device 100 that is detected by a sensor 110 or 112 (i.e., thermal or pressure activation); exposing the food safety device 100 to a specific type of liquid that is detected by a sensor 110 or 112 (i.e., liquid activation); or imparting a magnetic field on the food safety device 100 that is detected by the antenna 106 or a sensor 110 or 112 (i.e., magnetic activation). The activation can be for a period of days, months, or years, depending on the expected life cycle of the product 200. Thus, when a battery 104 is used to power the food safety device 100, it must be sized accordingly.

Figure 3A:
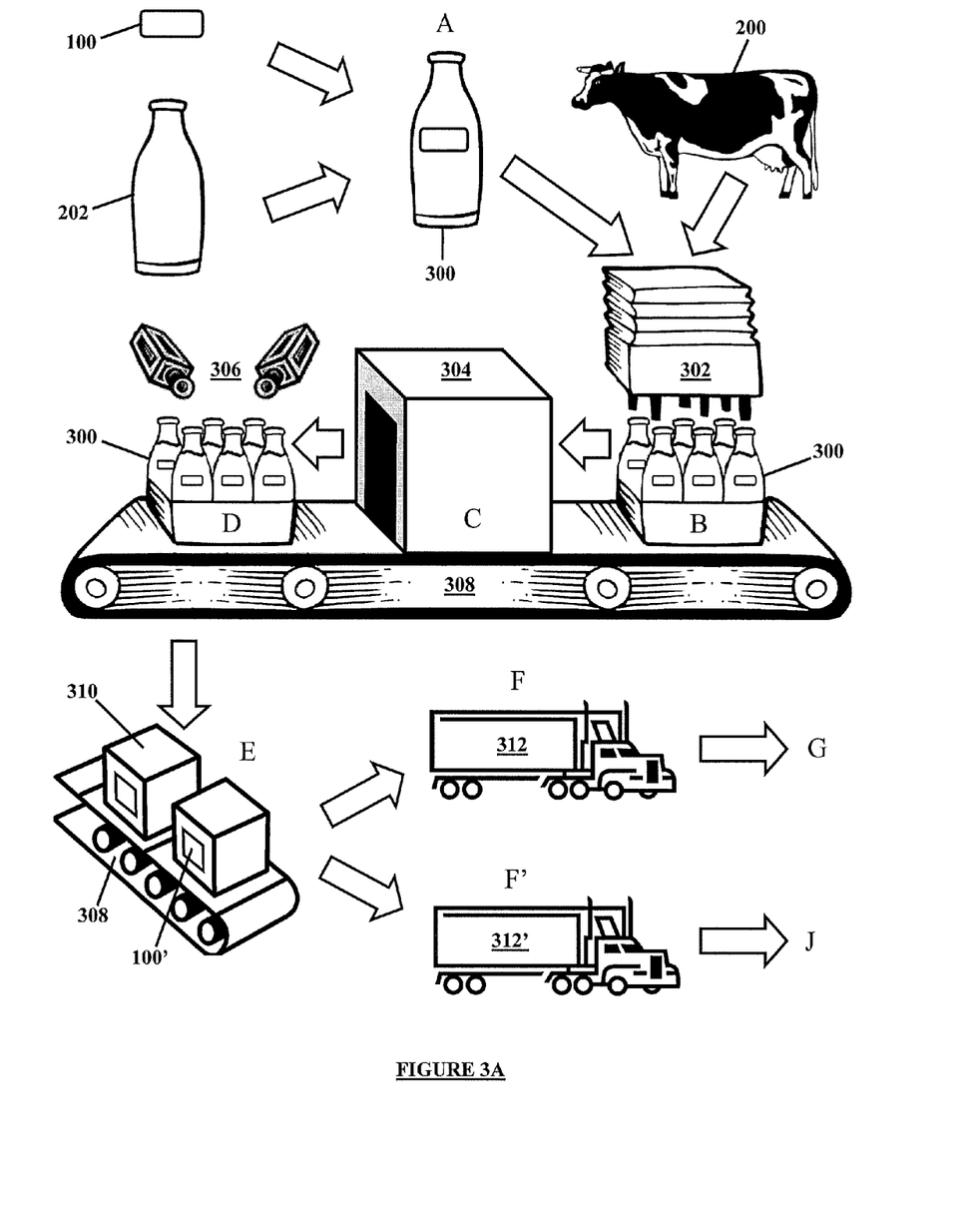
FIGS. 3A and 3B are schematic views illustrating a non-limiting embodiment of the use of the present invention throughout the life cycle of a product.
Figure 3B:
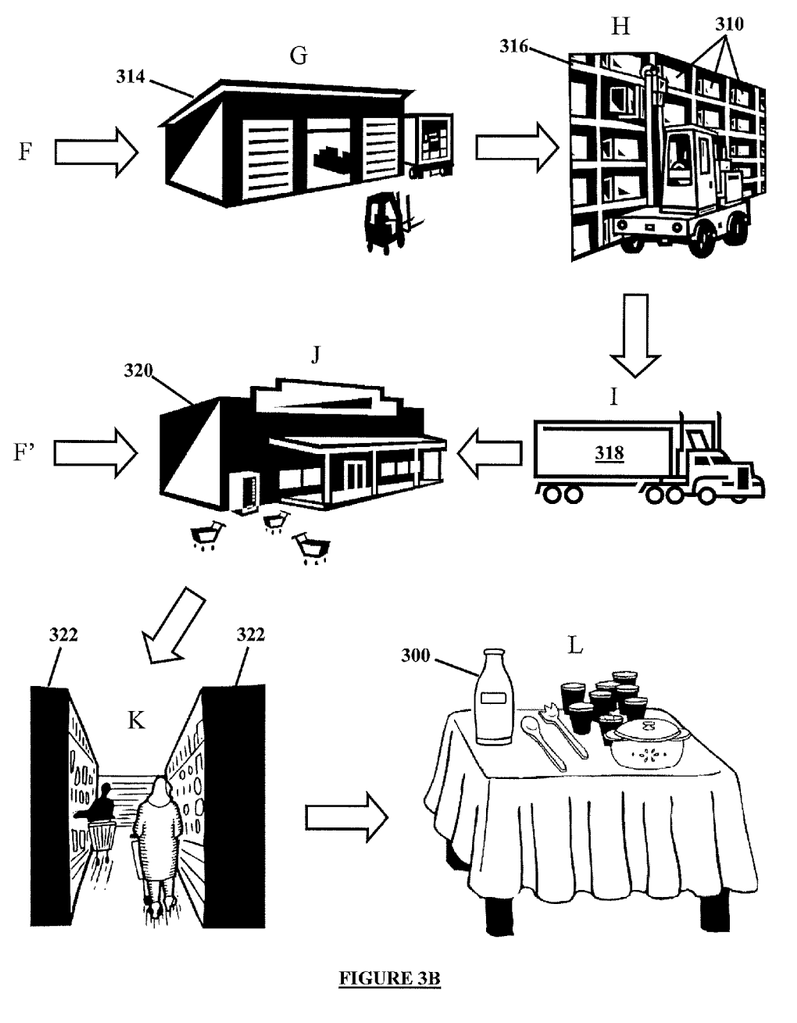

FIGS. 3A and 3B illustrate an exemplary embodiment of the present invention being implemented over the life cycle of a product 200 (e.g., milk). At step A, the food safety device 100 (e.g., an adhesive tag or label) is placed on a product container 202 (e.g., a bottle) to provide a tagged container 300. Data is stored on the food safety device 100 about the source of the container 202 (e.g., the identity of bottle manufacturer, the time and date of manufacture, the location of the manufacture, etc.) and the person or machine (not shown) that places the food safety device 100 on the container 202 (e.g., the serial number or unique ID of the machine, the time and date of placement, the machine location, etc.). In that way, if problems are subsequently discovered with product containers 202 from that source or with that machine, the containers from that source and/or handled by that machine can easily be identified with the data stored on the food safety device 100. Similarly, problems with the container 202 and/or with the application of the food safety device 100 to the container 202 can be tracked back to the source of the container 202 and/or the machine that applied the food safety device 100 to the container 202 using the data stored on the food safety device 100.

At step B, the product 200 is placed in the tagged container 300 by a packaging machine 302 (e.g., a bottle filler). At step C, the tagged container 300 and/or the product 200 are processed by a processing machine 304 (e.g., a pasteurizer) to prepare the product for consumption, such as by adding other components to it, mixing it, and/or treating it in a manner that will increase its shelf-life. And at step D, the tagged container 300 and the product 200 are inspected at an inspection station 306 (e.g., a leak detection system) to identify any problems with the tagged container 300 and/or the product 200.

The tagged container 300 and the product 200 are automatically carried from the packaging machine 302 to the processing machine 304, and from the processing machine 304 to the inspection station 306, by a conveyor system 308. And although only one packaging step (step B), one processing step (step C), and one inspection step (step D) are illustrated in FIG. 1A, any number of each of those steps may be provided in any order as required to package, process, and inspect the tagged container 300 and the product 200. For example, the product 200 may be processed by a second processing machine 304 (e.g., a separator) before being placed in a tagged container 300 by the packaging machine 302, and a corresponding inspection station 306 can be placed after each machine 302 and 304 (e.g., a fill level detection station after a bottle filler).

At steps B through D, data is stored on the food safety device 100 or centrally about each machine 302 and 304 and each inspection station 306 through which the tagged container 300 and the product 200 pass. That data identifies the specific machines 302 and 304 and the specific inspection stations 306 through which the tagged container 300 and the product 200 pass. That data may also identify the time and date that the tagged container 300 and the product 200 passed through those machines 302 and 304 and inspection stations 306, the facility at which those machines 302 and 304 and inspection stations 306 are located, and/or the assembly line on which those machines 302 and 304 and inspection stations 306 are located.

If a problem with the product 200 and/or product container 202 is identified at any point between steps A and D, the logic module 102 will identify that problem and cause one of the visual indicators (e.g., visual indicator 120) of the food safety device 100 to be displayed (e.g., illuminating a red LED), thereby providing a visual indication that a problem has occurred with that product 200 and/or product container 202 in case the product somehow makes it to an end user. The logic module 102 will also identify the date, time, and location at which that problem occurred and store that data so it can be used to identify any machine 302 or 304 that may be associated with that problem. That data can also be transmitted via the antenna 106 to an external computer that is controlling and/or monitoring the manufacturing/packaging process to immediately bring the problem to the manufacturer's/packager's attention, thereby allowing the problem to be quickly remedied. Moreover, the fact that there is a problem with the product 200 and/or product container 202 can be transmitted by the external computer or the food safety device 100 to a machine (not shown) that will remove that product from the manufacturing/packaging process so that problem product 200 and/or product container 202 will not ever make it to an end user. In that way, problems cannot only be quickly remedied so as to reduce the amount of down time for the manufacturing/packaging process, unsafe products 200 and/or product containers 202 can be quickly identified and removed from the manufacturing/packaging process so that unsafe products are not consumed by an end user.

At step E, the products 200 and product containers 202 that make it through steps A through D without a problem being identified are packaged for distribution. For example, those products 200 and product containers 202 are placed in boxes 310. A second food safety device 100' is placed on each box 310 so both the box 310 and its contents can be tracked and so the environment in which the box 310 and its contents are located can be monitored. Placing an additional food safety device 100' on the outside of the box 310 is particularly useful for monitoring the environment because the food safety devices 100 enclosed in the box may not be able to obtain accurate readings from within the box 310. Moreover, the additional food safety device 100' provides a source of additional data that can be used to verify the data stored on the food safety devices 100 on the products 200 and/or product containers 202 within each box 310.

The food safety device 100' placed on the box 310 stores data identifying each product 200 and/or product container 200 placed therein (i.e., the quantity and unique identification of each product 200 and/or product container 202) as well as all of the data for each of those products 200 and/or product containers 202 (i.e., the data stored on each food safety device 100 on each product 200 and/or product container 202). In that way, the food safety device 100' on the outside of the box 310 can be used to identify the contents of the box 310 as well as the condition of those contents. And both food safety devices 100 and 100' store data about the packaging process (e.g., the serial number of the machine, the time and date of packaging, the machine location, etc.) and the destination of the package (e.g., the address of a warehouse, the address of a retail store, etc.).

At step F or F', the boxes 310 are placed on a truck 312 or 312' that will transport the product 200 to its destination. That step completes the manufacturing/packaging process and begins the distribution process. Although the product 200 and/or product container 202 are no longer in the control of the manufacturer/packager after step F or F', the wireless data transmission functionality of the food safety devices 100 and 100' allows the manufacturer/packager to not only continue tracking the product 200 throughout the distribution process, it also allows the manufacturer/packager to continue monitoring the condition of the product 200 and/or product container 202 throughout the distribution process. In that way, the manufacturer/packager can make sure the product 200 does not become unsafe for consumption after it leaves their control. If the product 200 does become unsafe for consumption after it leaves the control of the manufacturer/packager, they can quickly identify the location (e.g., GPS coordinates) of that product 200 and recall it, replace it, or have it otherwise removed from its life cycle. Thus, the food safety devices 100 and 100' of the present invention allow manufacturers/packagers to maintain a great deal of control over their product 200 such that they can ensure the quality of the product 200 that reaches the end user.

To provide that level of control, the food safety devices 100 and 100' continue monitoring the condition and environment of the product 200 and/or product container 202 as the product 200 is transported to its next destination. The sensors 110-114 of the food safety devices 100 and 100' not only monitor the condition and environment of the product 200 and/or product container 202 as the product 200 is transported to its next destination, they can also identify the method of transportation. For example, one of the sensors 112 may include an accelerometer that measures acceleration. And the logic module 102 can correlate that acceleration with a specific mode of transportation (e.g., correlating large acceleration values to a plane, medium acceleration values to a truck, and small acceleration values to train) or with a specific event (e.g., correlating a sudden stop in acceleration to the container being dropped).

If the product 200 and/or product container 202 are damaged in transport, the manner in which that damage occurred (e.g., dropping the box 310, the box 310 toppling over, etc.) and the party who caused the damage can be identified with the data measured and stored by the food safety devices 100 and 100'. In that way, any costs associated with repairing or replacing the damaged product 200 and/or product container 202 can be allocated appropriately. Moreover, the damaged product 200 and/or product container 202 can be removed from its life cycle before it reaches the end user.

At step G, the truck 312 delivers the product 200 to a warehouse 314 where the boxes 310 are unloaded and stored on shelves 316 at step H. The warehouse 314 can utilize a computer system similar to that used by the manufacturer/packager to wirelessly communicate with the food safety devices 100 and 100' on the products 200 and/or product containers 202 and on the boxes 310. That data can be used to identify the location of the product 200 as well as its condition, making inventorying the product very simple. Again, if the product 200 and/or product container 202 are damaged at some point during those steps, the manufacturer/packager and/or the warehouse 314 can quickly identify that product 200 and/or product container 202 and remove it from its life cycle so a potentially unsafe product 200 does not make it to the end user.

At step I, the product 200 is placed on another truck 318 and transported from the warehouse 314 to a retail store 320. Both the warehouse 314 and the manufacturer/packager can use the food safety devices 100 and 100' to track the product and monitor the condition and environment of the product 200 and/or product container 202 as the product 200 is transported to its next destination. Again, if the product 200 and/or product container 202 are damaged during transport, the manufacturer/packager and/or the warehouse 314 can quickly identify the damaged product 200 and/or product container 202, identify how the damage occurred, identify the party responsible for the damage, and recall or repair the damaged product 200 and/or product container 202.

Instead of a truck 312 taking the product 200 to a warehouse 314 at step F before it is taken to a retail store 320 by another truck at step I, a truck 312' can take the product 200 directly to the retail store 320 at step F'.

At step J, the product 200 is unpackaged and placed on the shelves 322 of the retail store 320 where it can be purchased by an end user at step K. The retail store 320 can utilize a computer system similar to that used by the manufacturer/packager and/or the warehouse 314 to wirelessly communicate with the food safety devices 100 on the products 200 and/or product containers 202. That data can be used to identify the location of the product 200 as well as its condition, making inventorying the product very simple. Again, if the product 200 and/or product container 202 are damaged at some point during that step, the manufacturer/packager, the warehouse 314, and/or the retail store 320 can quickly identify that product 200 and/or product container 202 and remove it from its life cycle so a potentially unsafe product 200 does not make it to the end user.

At step L, the product 200 makes it to the end user in its tagged container 300. Using the wireless data transmission technology of the food safety device 100, the manufacturer/packager, the warehouse 314, and/or the retail store 320 can locate the product 200 and recall it, replace it, or instruct the end user to dispose of it if the product 200 is discovered at any point to be unsafe for consumption. The manufacturer/packager, the warehouse 314, and/or the retail store 320 can also send a signal to the food safety device 100 to trigger any one of its indicators (e.g., visual indicators 116-124, tactile indicators, and/or audible indicators) at any point in its life cycle to alert the end user that it is potentially unsafe.

Using the functionality of the present invention, food producers, warehouses, retail stores, and the Food and Drug Administration (FDA) can track products, rotate aging products, avoid having to throw away products, and prevent underhanded selling of products having health issues, all of which reduce overhead expenses. Moreover, the wireless data exchange functionality of the present invention can be used by end users to access product-specific information on their cell phones while standing in a retail store 320 with that product 200 in hand. And the manufacturer/packager, the warehouse 314, and/or the retail store 320 can use the data to identify the exact location where the products 200 were consumed by the end user (e.g., the location where the end user's lives), which can be used advantageously for marketing and/or distribution purposes.

In addition, the food safety device 100 can generate a variety of predetermined or custom reports based on the stored data. For example, a report can be generated that indicates the maximum, minimum, and average temperature of a product 200 during its life cycle as well as the dates and times at those temperatures occurred. The report can be displayed on an LCD of the food safety device 100 or transmitted via the antenna 106 to printer. The data can also be transmitted via the antenna 106 to a processor or computer at a local or central location that can generate the reports for that particular product 200 or for a variety of products 200.

The data stored on the food safety device 100 can also be used to determine the time it takes for a product to go from being manufactured/packaged to a retail store 320 or end user for a particular manufacturer/packager, warehouse 314, or retail store 320. Or, that data can be used to determine the time that a certain type of product 200 is below a predetermined temperature; to determine the distance travelled by a given product 200 (e.g., from origin to end user, from one warehouse 314 to another, from warehouse 314 to retail store 320, from retail store 320 to end user, etc.); or to ensure and confirm that the product has been handled in accordance with governmental regulations, such as the Food Safety Modernization Act.

Although the present invention has been described for use with perishable products, other suitable uses will be apparent. For example, the food safety device 100 can be used as a tag to track wildlife, thereby providing invaluable environmental data. That could be achieved by catch and release to track animals such as tuna or salmon in the wild. It could also be used on fish farms to assure the fish are raised in the proper environment to maintain a safe food supply.

The invention has been described in non-limiting illustrative embodiments, without intending to limit the scope or teaching of the invention, as a food safety device having a single flexible substrate with a front and a rear. Various flexible components are located on the substrate, including a battery, sensor, display, antenna, logic, and/or bar code. The sensor is preferably located on the rear of the substrate and the remaining elements are preferably provided at the front of the substrate. However, one or all of the components can be located on the rear of the substrate, with the display being visible at the front of the substrate. However, one or all the components can instead be located on the front of the substrate. An adhesive is located on the rear of the substrate, and can also be provided on the components located on the rear of the substrate. The adhesive binds the substrate to a product or its packaging/container. The entire food safety device is flat and preferably relatively thin (0.5-5 mm). The food safety device can also be configured to be integral to a container or packaging (wrapper).

The sensor detects the conditions of the product and/or the surrounding conditions. The sensed conditions can be processed during the entire life cycle of the product, or at discrete stages, including as the product progresses from the harvesting, processing, manufacture, distribution, storage, and delivery to the food store and finally to the end user consumer. That information can be stored in a memory on the food safety device, and/or can be wirelessly transmitted to a reader (such as one having an antenna and processor; and located at one or more of the stages) for storage at the reader or a local processing device or at a remote central processing device in communication with the reader.

Additional information can be associated with the food safety device and stored at the food safety device (received from the reader/transmitter at one or more of the stages) or remote processing device, such as the processing and food processing conditions (which may be detected by the sensor or by a remote sensor) of temperature or the like. Each safety device can be associated with a unique identification code (ID) that identifies the safety device, so that the conditions and location of the safety device can be tracked by the remote processing device. And, the location of the safety device can be identified in the event that similarly-processed food items are determined to be contaminated or unsafe.

In another illustrative embodiment of the invention, the device can be a peel-and-stick radiation sensor (such as a Geiger counter) that can be attached (such as by an adhesive) to a product, item or thing. When utilized with food, for instance, the sensor is activated and then the device is stuck with its adhesive back to food staples such as food boxes, produce, food packaging, and/or food containers. The sensor can change color or otherwise indicate a radiation level, such as due to surface, airborne, direct or indirect radiation. The various levels of radiation safety can be set in advance during manufacture. A bar code can be combined with the sensor. The bar code can be associated with the device (such as a unique ID). Any detected sensor level can be scanned by a smart phone or bar code reader and sent to a centralized database for tracking, safety, treatment and/or scientific study. The bar code can be built into the sensor or the bar code can appear for scanning when activated by predetermined or unsafe levels of radiation. The device can be about 1-2 inches wide and relatively flat (about 1-5 mm). The device can be used on food products and other applications, such as office buildings, doorways, vehicles, and furniture. It can be attached by a strap to clothing or worn like a wristwatch, put on shoes or vehicle tires.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. For example, instead of wirelessly transmitting data to external systems via the antenna 106, that data can be read from a bar code displayed by one of the visual indicators 126. Therefore, it is not desired to limit the invention to the specific examples disclosed or the exact construction and operation shown and described. Rather, all suitable modifications and equivalents may be resorted to, falling within the scope of the invention.

What is claimed is:

1. A food safety device for placement on a product comprising:
  a light sensor configured to detect light to which the product is exposed;
  one or more visual indicators configured to display a visual indication of freshness and/or safety of the product;
  an antenna configured to transmit and receive data regarding the detected light to which the product is exposed and the freshness and/or safety of the product; and
  a logic module configured to execute programmable logic to determine the freshness and/or safety of the product from the detected light to which the product is exposed, to cause the one or more visual indicators to display a visual indication of the freshness and/or safety it determines, and to transmit and receive data regarding the detected light to which the product is exposed and the freshness and/or safety of the product via the antenna,
  wherein said light sensor comprises a photovoltaic solar cell that is configured to detect the light to which the product is exposed and to power the one or more sensors, the one or more visual indicators, the antenna, and the logic module.

2. The food safety device of claim 1, further comprising a battery that is printed on the food safety device and is configured to power the light sensor, the one or more visual indicators, the antenna, and the logic module.

3. The food safety device of claim 1, further comprising:
  at least one first sensor configured to detect the product's environment; and
  at least one second sensor configured to detect the condition of the product,
  and wherein said logic module is configured to determine the freshness and/or safety of the product from the detected light, the product's environment and the product condition.

4. The food safety device of claim 3, wherein
  the at least one first sensor detects an amount of at least one of temperature, pressure, light exposure, humidity, vibration, shock, acceleration, radiation, hazardous chemicals, toxins, and food borne pathogens in the product's environment; and
  the at least one second sensor detects an amount of at least one of temperature, pressure, light exposure, humidity, radiation, hazardous chemicals, toxins, and food borne pathogens at the product.

5. The food safety device of claim 1, wherein the logic module is further configured to execute programmable logic to identify a current location of the product on which the food safety device is placed and to transmit that location to another device via the antenna.

6. The food safety device of claim 1, wherein the logic module is further configured to execute programmable logic to identify a current location of the product on which the food safety device is placed and to transmit that location to another device via the antenna.

7. The food safety device of claim 1, wherein the logic module is further configured to execute programmable logic to receive and store data about at least one of a machine that packages the product, a machine that processes the product, and an inspection station where the product is inspected.

8. The food safety device of claim 1, wherein the light sensor, the one or more visual indicators, the antenna, and the logic module are provided on a substantially flat label that is configured to be attached to the product and/or packaging in which the product is placed.

9. The food safety device of claim 1, wherein the light sensor, the one or more visual indicators, the antenna, and the logic module are provided as part of packaging in which the product is placed.

10. The food safety device of claim 1, wherein the one or more sensors comprises a first sensor configured to measure temperature, said device further comprising a clocking circuit configured to determine time, and wherein said logic module is configured to determine the freshness and/or safety of the product based on an amount of time that the product is at the measured temperature.

11. A method for making a food safety device comprising the steps of:
    providing a light sensor configured to measure light to which the product is exposed;
    providing one or more visual indicators configured to display a visual indication of freshness and/or safety of the product;
    providing an antenna configured to transmit and receive data regarding measured light to which the product is exposed and the freshness and/or safety of the product; and
    providing a logic module configured to execute programmable logic to determine the freshness and/or safety of the product from the measured light to which the product is exposed, to cause the one or more visual indicators to display a visual indication of the freshness and/or safety it determines, and to transmit and receive data regarding the measured light to which the product is exposed and the freshness and/or safety of the product via the antenna,
    wherein said light sensor comprises a photovoltaic solar cell that is configured to measure the light to which the product is exposed and to power the light sensor, the one or more visual indicators, the antenna, and the logic module.

12. The method of claim 11, further comprising the step of printing a battery on the food safety device that is configured to power the light sensor, the one or more visual indicators, the antenna, and the logic module.

13. The method of claim 11, further comprising one or more sensors include:
    at least one first sensor configured to measure the product's environment; and
    at least one second sensor configured to measure the condition of the product.

14. The method of claim 13, wherein
    the at least one first sensor measures an amount of at least one of temperature, pressure, light exposure, humidity, vibration, shock, acceleration, radiation, hazardous chemicals, toxins, and food borne pathogens in the product's environment; and
    the at least one second sensor measures an amount of at least one of temperature, pressure, light exposure, humidity, radiation, hazardous chemicals, toxins, and food borne pathogens at the product.

15. The method of claim 11, wherein the logic module is further configured to execute programmable logic to identify a current location of the product on which the food safety device is placed and to transmit that location to another device via the antenna.

16. The food safety device of claim 11, wherein the logic module is further configured to execute programmable logic to identify a current location of the product on which the food safety device is placed and to transmit that location to another device via the antenna.

17. The food safety device of claim 11, wherein the logic module is further configured to execute programmable logic to receive and store data about at least one of a machine that packages the product, a machine that processes the product, and an inspection station where the product is inspected.

18. The method of claim 11, wherein the light sensor, the one or more visual indicators, the antenna, and the logic module are provided on a substantially fiat label that is configured to be attached to the product and/or packaging in which the product is placed.

19. The method of claim 11, wherein the light sensor, the one or more visual indicators, the antenna, and the logic module are provided as part of packaging in which the product is placed.

* * * * *